United States Patent
Becker et al.

(10) Patent No.: US 10,354,421 B2
(45) Date of Patent: Jul. 16, 2019

(54) APPARATUSES AND METHODS FOR ANNOTATED PEPTIDE MAPPING

(71) Applicant: Protein Metrics Inc., Cupertino, CA (US)

(72) Inventors: Christopher Becker, Redwood City, CA (US); Marshall Bern, San Carlos, CA (US); Nicholas Bern, New York City, NY (US); Yong Joo Kil, Fremont, CA (US); Richard Seipert, Fremont, CA (US); Michael Taejong Kim, South San Francisco, CA (US)

(73) Assignee: Protein Metrics Inc., Cupertino, CA (US)

(*) Notice: Subject to any disclaimer, the term of this patent is extended or adjusted under 35 U.S.C. 154(b) by 483 days.

(21) Appl. No.: 15/066,871

(22) Filed: Mar. 10, 2016

(65) Prior Publication Data

US 2016/0267220 A1   Sep. 15, 2016

Related U.S. Application Data

(60) Provisional application No. 62/131,148, filed on Mar. 10, 2015.

(51) Int. Cl.
| | | |
|---|---|---|
| *G01N 33/48* | (2006.01) | |
| *G06T 11/20* | (2006.01) | |
| *G16B 45/00* | (2019.01) | |
| *G16B 40/00* | (2019.01) | |

(52) U.S. Cl.
CPC ........... *G06T 11/206* (2013.01); *G16B 40/00* (2019.02); *G16B 45/00* (2019.02)

(58) Field of Classification Search
None
See application file for complete search history.

(56) References Cited

U.S. PATENT DOCUMENTS

| | | |
|---|---|---|
| 4,464,650 A | 8/1984 | Eastman et al. |
| 4,558,302 A | 12/1985 | Welch |
| 4,814,764 A | 3/1989 | Middleton |
| 5,343,554 A | 8/1994 | Koza et al. |
| 5,995,989 A | 11/1999 | Gedcke et al. |
| 6,094,627 A | 7/2000 | Peck et al. |
| 6,393,393 B1 | 5/2002 | Kawahara |
| 6,535,555 B1 | 3/2003 | Bordes et al. |
| 6,798,360 B1 | 9/2004 | Qian et al. |
| 6,906,320 B2 | 6/2005 | Sachs et al. |
| 7,006,567 B2 | 2/2006 | Frossard et al. |
| 7,283,684 B1 | 10/2007 | Keenan |
| 7,283,937 B2 | 10/2007 | Goldberg |

(Continued)

FOREIGN PATENT DOCUMENTS

WO   WO2011/127544 A1   10/2011

OTHER PUBLICATIONS (BiopharmaLynx: A New Bioinformatics Tool for Automated LC/MS Peptide Mapping Assignment; Sep. 2008, 1-6).*

(Continued)

*Primary Examiner* — Larry D Riggs, II
(74) *Attorney, Agent, or Firm* — Shay Glenn LLP

(57) ABSTRACT

Methods and apparatuses for the analysis of mass spectroscopic (MS) data as well as ultraviolet (UV) absorption data. In particular, described herein are tools and methods to assist in generating annotated peptide maps from a raw MS data.

15 Claims, 13 Drawing Sheets

(56) References Cited

U.S. PATENT DOCUMENTS

| | | |
|---|---|---|
| 7,297,940 B2 | 11/2007 | Bern |
| 7,400,772 B1 | 7/2008 | Keenan |
| 7,402,438 B2 | 7/2008 | Goldberg |
| 7,429,727 B2 | 9/2008 | Bern |
| 7,496,453 B2 | 2/2009 | Chau |
| 7,680,670 B2 | 3/2010 | Lamblin et al. |
| 7,979,258 B2 | 7/2011 | Goldberg et al. |
| 8,004,432 B2 | 8/2011 | Kawato |
| 8,077,988 B2 | 12/2011 | Donoho |
| 8,108,153 B2 | 1/2012 | Bern |
| 8,428,889 B2 | 4/2013 | Wright |
| 8,511,140 B2 | 8/2013 | Gorenstein et al. |
| 8,598,516 B2 | 12/2013 | Sapargaliyev et al. |
| 8,645,145 B2 | 2/2014 | Subbaraman et al. |
| 2002/0068366 A1 | 6/2002 | LaDine et al. |
| 2003/0031369 A1 | 2/2003 | Le Pennec et al. |
| 2004/0102906 A1 | 5/2004 | Roder |
| 2004/0160353 A1 | 8/2004 | Cirillo et al. |
| 2005/0047670 A1 | 3/2005 | Qian et al. |
| 2008/0010309 A1 | 1/2008 | Sugita |
| 2008/0260269 A1 | 10/2008 | Thiagarajan |
| 2010/0124785 A1 | 5/2010 | Bern |
| 2010/0288917 A1 | 11/2010 | Satulovsky et al. |
| 2010/0288918 A1 | 11/2010 | Satulovsky |
| 2011/0093205 A1 | 4/2011 | Bern |
| 2012/0047098 A1 | 2/2012 | Reem |
| 2012/0245857 A1 | 9/2012 | Lee et al. |
| 2013/0080073 A1 | 3/2013 | de Corral |
| 2013/0144540 A1 | 6/2013 | Bern et al. |
| 2013/0226594 A1 | 8/2013 | Fuchs et al. |
| 2013/0262809 A1 | 10/2013 | Wegener |
| 2013/0275399 A1 | 10/2013 | Amit et al. |
| 2013/0289892 A1 | 10/2013 | Satoh |
| 2014/0045273 A1 | 2/2014 | Cerda et al. |
| 2014/0164444 A1 | 6/2014 | Bowen et al. |
| 2015/0319268 A1 | 11/2015 | Callard et al. |
| 2016/0077926 A1 | 3/2016 | Mutalik et al. |
| 2016/0099723 A1 | 4/2016 | Kletter |
| 2016/0215028 A1 | 7/2016 | Mutharia et al. |
| 2016/0315632 A1 | 10/2016 | Kletter |
| 2017/0155403 A1 | 6/2017 | Kletter |

OTHER PUBLICATIONS (MassLynx 4.1 Getting Started Guide, Waters Corp. 2005).*

(QuanLynx User's Guide, Version 4.0, Feb. 2002).*

Schreiber et al.; Using PeakView(TM) software with the XIC manager for screening and identification with high confidence based on high resolution and accurate mass LC-MS/MS; AB Sciex; Food & Environmental; (Pub. # 2170811-03); 5 pgs.; Apr. 2, 2011.

Thermo Fisher Scientific, Inc.; Thermo Xcaliber: Qualitative Analysis (User Guide); Revision B; 290 pgs.; Sep. 2010.

Valot et al.; MassChroQ: A versatile tool for mass spectrometry quantification; Proteomics; 11(17); 23 pgs.; Sep. 2011.

VanBramer; An Introduction to Mass Spectrometry; Wider University; 38 pgs.; © 1997; (revised) Sep. 2, 1998.

Yang et al.; Detecting low level sequence variants in recombinant monoclonal antibodies; mAbs 2 (3); pp. 285-298; May/Jun. 2010.

Ziv et al.; A universal algorithm for sequential data compression; IEEE Trans. on Information Theory; IT-23(3); pp. 337-343; May 1977.

Ziv et al.; Compression of individual sequences via variable-rate coding; IEEE Trans. on Information Theory; IT-24(5); pp. 530-536; Sep. 1978.

Becker et al.; U.S. Appl. No. 14/306,020 entitled "Interactive Analysis of Mass Spectrometry Data," filed Jun. 16, 2014.

Becker et al. U.S. Appl. No. 15/583,752 entitled "Interactive analysis of mass spectrometry data," filed May 1, 2017.

Bern et al., U.S. Appl. No. 15/881,698 entitled "Methods and apparatuses for determining the intact mass of large molecules from mass spectrographic data," filed Jan. 26, 2018.

* cited by examiner

APPARATUSES AND METHODS FOR ANNOTATED PEPTIDE MAPPING

CROSS REFERENCE TO RELATED APPLICATIONS

This application claims priority to U.S. Provisional Patent Application No. 62/131,148, filed Mar. 10, 2015, titled "APPARATUSES AND METHODS FOR ANNOTATED PEPTIDE MAPPING," and is herein incorporated by references in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein generally relate to tools for the analysis and interpretation of analytic chemical data, and particularly mass spectrometry (MS) data. For example, described herein are tools for the alignment of multiple chromatograms (UV fluorescence, UV absorption, mass spectrometry total ion chromatogram, etc.), as well as tools for annotating data such as MS data, including annotation of peptide maps. These tools may also be used for detached glycan analysis, including annotation and comparison.

BACKGROUND

Peptide mapping is a valuable approach to combine positional quantitative information with topographical and domain information of proteins. In particular, annotated peptide mapping, particularly of protein-coding genes, is a useful procedure and a critical goal of many genome sequencing projects and biomedical and biopharmaceutical research efforts. Despite advances in computational gene finding, the comprehensive annotation of proteins, including clinically relevant proteins remains challenging.

A tandem mass spectrum can be viewed as a collection of fragment masses from a single peptide (e.g., eight to 30 amino acids from an enzymatically digested protein). This set of mass values is a partial "fingerprint" that may be used to help identify the peptide. The spectra are usually not analyzed de novo. Instead, they are compared against peptides from a database of known proteins, and may be used in in conjunction with other sources of analytic information to converge on an interpretation of the large amount of data provided by MS. For example, additional data may include chromatography (UV) data. Much research has been devoted to improving the accuracy of this search by refining scoring, improving search speed, and handling post-translational modifications.

Due to the complexity of proteins and their biological production, characterization of protein pharmaceuticals ("biologics") poses much more demanding analytical challenges than do small molecule drugs. Biologics are prone to production problems such as sequence variation, misfolding, variant glycosylation, and post-production degradation including aggregation and modifications such as oxidation and deamidation. These problems can lead to loss of safety and efficacy, so the biopharmaceutical industry would like to identify and quantify variant and degraded forms of the product down to low concentrations, plus obtain tertiary structure information.

In particular, in the pharmaceutical field, there is a need to characterize recombinantly produced protein molecules in new product development, biosimilar (generic) product development, and in quality assurance for existing products. Primary structure analyses can include total mass (as measured by MS), amino acid sequence (as measured by orthogonal peptide mapping with high resolution MS and MS/MS sequencing), disulfide bridging (as measured by non-reducing peptide mapping), free cysteines (as measured by Ellman's or peptide mapping), and thioether bridging (as measured by peptide mapping, SDS-PAGE, or CGE). Higher order structure can be analyzed using CD spectroscopy, DSC, H-D-exchange, and FT-IR. Glycosylation requires identification of glycan isoforms (by NP-HPLC-ESI-MS, exoglycosidase digestion, and/or MALDI TOF/TOF), sialic acid (by NP-HPLC, WAX, HPAEC, RP-HPLC) and aglycolsylation (by CGE and peptide mapping). Heterogeneity analyses must take into consideration C- and N-terminal modifications, glycation of lysine, oxidation, deamidation, aggregation, disulfide bond shuffling, and amino acid substitutions, insertions and deletions. The large variety of assays and techniques gives some idea of the daunting analytical challenge. Mass spectrometry (MS) can cover most of the physicochemical properties required for molecular analysis, but may be powerfully combined with other sources of information, including other modalities (including UV data).

Unfortunately, MS data is often complex and difficult to interpret. MS generally relies on automatic data analysis, due to the huge numbers of spectra (often >10,000/hour), the high accuracy of the measurements (often in the 1-10 ppm range), and the complexity of spectra (100 s of peaks spanning a dynamic range >1000). There are a large number of programs for "easy" MS-based proteomics, for example, SEQUEST, Mascot, X!Tandem, etc., but these programs were not designed for deep analysis of single proteins, and are incapable of difficult analytical tasks such as characterizing mutations, glycopeptides, or metabolically altered peptides. Moreover, the programs just named are all identification tools and must be coupled with other programs such as Rosetta Elucidator (now discontinued), Scaffold, or Thermo Sieve for differential quantification. There are also specialized tools such as PEAKS for de novo sequencing, along with a host of academic tools. The confusing array of software tools poses an obstacle to biotech companies adopting MS-based assays.

Described herein are methods and tools (including apparatuses) that may aid in the analysis of proteins, and in particular may allow protein mapping and particularly automatic and manual annotation of protein maps, in a manner that is accurate and efficient.

SUMMARY OF THE DISCLOSURE

The methods and tools described herein, including software, firmware and hardware, are generally directed to annotation and mapping of analytic chemistry data, including in particular mass spectrometry (MS) data, and may include in particular automated processing and/or annotation of peptide mapping. These method and tools may allow formation of an annotated peptide map as well as simultaneous alignment and comparison of a plurality (e.g., up to 10 or more) of peptide maps, and create figures and tables based on this analysis. For example, the tools and methods described herein may be configured to perform time correlation, allowing interaction and visualization of MS at different times, may perform non-linear time alignment of different spectral datasets (e.g., MS data), including setting a smooth baseline, may detect and annotate elution peaks and identify features of peaks, may computes peak areas for accurate relative quantitation, and may automatically identify candidate peaks or regions for additional analysis. These tools and methods generally provide interactive views and display of all or some of the analysis.

For example, described herein are methods for the automated analysis and annotation of peptide maps that may include: importing candidate peptides related to a target protein, concurrently displaying a chromatographic trace, a listing of candidate peptides, and a listing of peaks from the chromatographic trace, automatically annotating peaks of the chromatograph using the candidate peptides based on mass accuracy and/or other quality characteristics, and displaying the annotated peaks concurrently with the chromatographic trace, listing of candidate peptides and listing of peaks from the chromatographic trace. The methods may also include concurrently displaying a plurality of additional chromatographic traces, and in some variations, aligning the plurality of additional chromatographic traces with a reference chromatographic trace.

The apparatuses and methods may be configured to allow a user to manually annotate peaks of the chromatograph, and/or to modify the chromatographic trace display. For example, the user may manually (or the apparatus may automatically) adjust the baseline of the chromatographic (e.g., UV, TIC, etc.) trace.

Also described herein are time correlation methods and tools, including apparatuses, which explicitly include devices and systems, including software, firmware and hardware, including non-transitory computer-readable storage medium storing a set of instructions capable of being executed by a processor. Time correlation may be used to correlate the peak in a chromatogram with mass/charge data (e.g., MS1 data). For example, a method of displaying a correlation between a candidate molecule and a candidate chromatographic peak by time correlation may include: defining a time period from a chromatograph corresponding to a region of peak signal intensity; determining intensity values at a mass/charge segment for each of a plurality of times within the time period; comparing a time course of the intensity values for the mass/charge segment over the time period to the time course of the signal intensity over the region of peak signal intensity; and labeling a visual representation of the mass/charge segment in a mass spectrogram with an indicator of a score of the correlation. The time period may be automatically or manually defined.

The method may also include selecting the mass/charge segment to be analyzed from within a mass/charge region (e.g., the MS1 data) by having an intensity that is greater than a threshold, e.g., having an intensity that is greater than a threshold percentage of a maximum value of the intensity within the region of mass/charge.

Also described herein are apparatuses including a non-transitory computer-readable storage medium storing a set of instructions capable of being executed by a processor, that when executed by the processor causes the processor to perform time correlation, for example, to: define a time period from a chromatograph corresponding to a region of peak signal intensity; determine intensity values at a mass/charge segment for each of a plurality of times within the time period; compare a time course of the intensity values for the mass/charge segment over the time period to the time course of the signal intensity over the region of peak signal intensity; and label a visual representation of the mass/charge segment in a mass spectrogram with an indicator of a score of the correlation.

Also described herein are method and apparatuses that align multiple chromatographic traces using a time warping method (nonlinear alignment). For example, a method of displaying a plurality of chromatographic traces to allow visual inspection of the traces may include: generating a first time transformed trace of a first chromatographic trace by comparing signal intensities from the first chromatographic trace with signal intensities of a reference chromatographic trace and adjusting the time values from the first chromatographic trace to correspond to time values of similar signal intensities of the reference chromatographic trace; identifying a plurality of reference anchor points from the reference chromatographic trace, wherein the reference anchor points include one or more points of peak signal intensity; determining a corresponding anchor point for each of the reference anchor points from the first time transformed trace; generating a second transformed first chromatographic trace from the time values for each of the corresponding anchor points by scaling time values from the first chromatographic trace between time-adjacent pairs of corresponding anchor points; and displaying the second transformed first chromatographic trace aligned with the reference chromatographic trace.

Generating the first time transformed trace may include comparing dividing the first chromatographic trace and the reference chromatographic trace into a plurality of sub-regions for comparison. The step of generating the second transformed first chromatographic trace from the time values for each of the corresponding anchor points may comprise linearly scaling time values from the first chromatographic trace between time-adjacent pairs of corresponding anchor points.

The step of identifying the plurality of anchor points may comprise identifying local maximum and flanking minimum intensity values from the reference chromatographic trace forming a peak in the reference chromatographic trace.

In general, displaying may comprise presenting the second transformed first chromatographic trace immediately above or below the reference chromatographic trace. For example, displaying may comprise presenting the second transformed first chromatographic trace on top of the reference chromatographic trace or slightly displaced above the reference chromatographic trace. In some variations, displaying comprises displaying the reference chromatographic trace in a different color than the second transformed first chromatographic trace.

Also described herein are apparatuses including non-transitory computer-readable storage medium storing a set of instructions capable of being executed by a processor, that when executed by the processor causes the processor to: generate a first time transformed trace of a first chromatographic trace by comparing signal intensities from the first chromatographic trace with signal intensities of a reference chromatographic trace and adjusting the time values from the first chromatographic trace to correspond to time values of similar signal intensities of the reference chromatographic trace; identify a plurality of reference anchor points from the reference chromatographic trace, wherein the reference anchor points include one or more points of peak signal intensity; determine a corresponding anchor point for each of the reference anchor points from the first time transformed trace; generate a second transformed first chromatographic trace from the time values for each of the corresponding anchor points by scaling time values from the first chromatographic trace between time-adjacent pairs of corresponding anchor points; and display the second transformed first chromatographic trace aligned with the reference chromatographic trace.

BRIEF DESCRIPTION OF THE DRAWINGS

FIG. 3A shows an entire UV chromatograph trace. FIG. 3B shows the start of the UV trace, including the baseline error; the apparatuses described herein may be used to manually or automatically adjust the baseline, as shown in FIG. 3C for the start of the UV trace. FIG. 3D shows the end of the UV trace, also exhibiting baseline drift, which is shown corrected in FIG. 3E.

DETAILED DESCRIPTION

Figure 1:
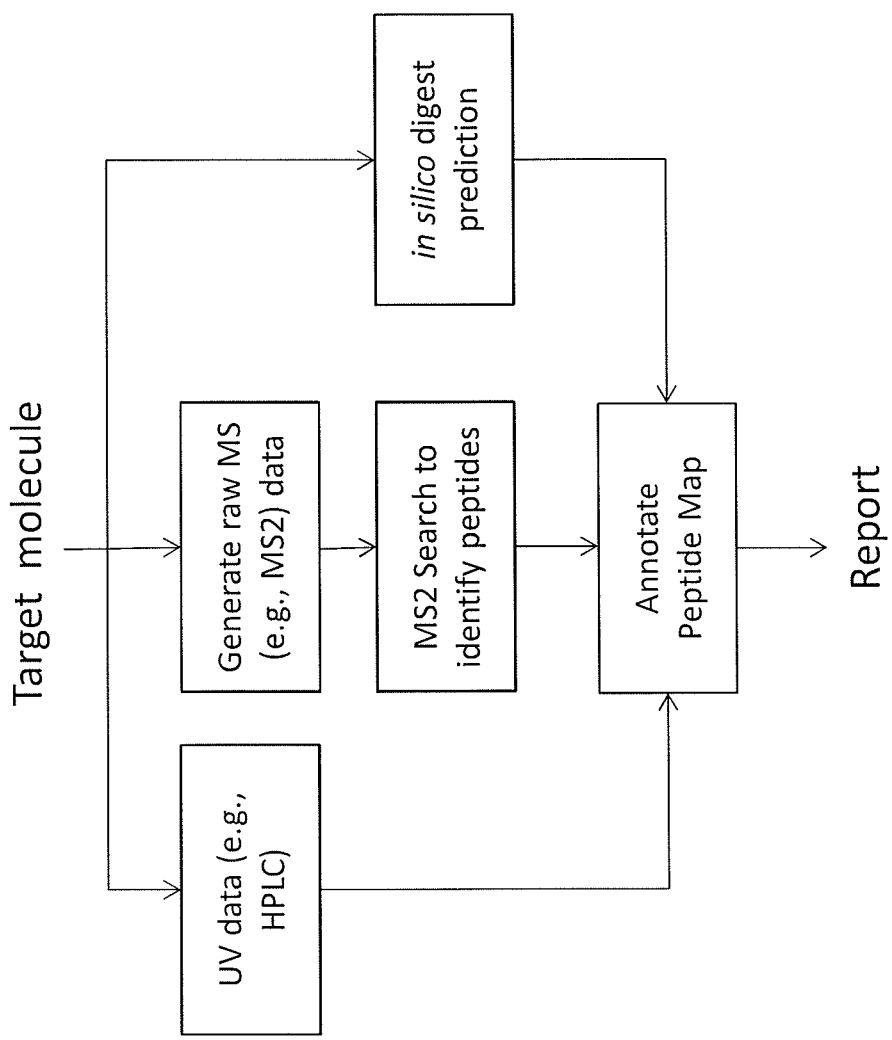
FIG. 1 is an overview of a method for creating and annotating (including automatically annotating) a peptide map as described herein.

In general, the methods and apparatuses described herein may be used to examine and interpret analytic chemistry data, such as (but not limited to) mass spectrometry (MS) data. For example, the tools and methods described herein may be used to generate a peptide map from a raw MS data file (such as a raw data from Thermo Scientific mass spectrometers, e.g., Thermo RAW LC-MS/MS, tandem mass spectrometry, data files).

Although the disclosure, including examples, described herein focuses primarily on MS of peptides and peptide analysis, including mapping and annotation of peptides, these methods and apparatuses described herein are not limited to peptides. In general, the methods and apparatuses described herein may be applied (and/or adapted) for use with any type or class of chemical that can be analyzed by mass spectroscopy, including in particular biological macromolecules such as glycans, metabolites, oligosaccharides, saporins, saponins, etc. For example, the methods and apparatuses described herein may be used for glycan analysis, including detached glycans as part of a detached glycan analysis. Glycans can be identified and annotated based on their mass (e.g., MS1). In addition, whether or not individual glycans have been annotated, multiple detached glycan chromatographic traces may be quantitatively compared and aligned as descried herein for peptide maps. The methods and apparatuses described herein may are not limited to MS data, but may be used with (and make use of) other analytical technologies such as the liquid chromatography, capillary electrophoresis and the like, which may provide additional or alternative chromatographic traces.

As used herein, "sequence variant" refers to any chemical change in a protein, peptide or peptide fragment relative to its wildtype counterpart. Sequence variants can include single or double amino acid substitutions, single amino acid insertions, single amino acid deletions, truncations, as well as oxidation, deamidation, glycosylation, and the like.

As used herein, the term "Mass Spectrometry" (MS) refers to a technique for measuring and analyzing molecules that involves ionizing or ionizing and fragmenting a target molecule, then analyzing the ions, based on their mass/charge ratios (m/z), to produce a mass spectrum that serves as a "molecular fingerprint". There are several commonly used methods to determine the mass to charge ratio of an ion, some measuring the interaction of the ion trajectory with electromagnetic waves, others measuring the time an ion takes to travel a given distance, or a combination of both.

As used herein, the term "sample" is used in its broadest sense, and may include a specimen or culture, of natural or synthetic origin.

As used herein, "protein" refers to a polymer of amino acids (whether or not naturally occurring) linked via peptide bonds. For the purposes of the present disclosure, a protein is the complete product, prior to any enzymatic digestion or fragmentation, that is to be subjected to analysis by mass spectrometry.

A "peptide," as used herein, refers to one or more members of the mixture produced by controlled digestion of a protein. Typically, the peptide mixture is a product of digestion of the protein with a proteolytic enzyme, however other methods of controlled digestion are contemplated. It is preferred that the digestion mechanism cleave the protein at positions in response to the presence of specific amino acids. Due to incomplete digestion by the enzyme or other mechanism, the mixture of digestion products (i.e. peptides) can include the undigested protein, which in this situation would also be a peptide.

Finally, as used herein the term "fragment" or "peptide fragment" refers to the products of fragmentation within a mass spectrometer.

In general, the intensity of signals in traces processed as described herein can refer to the total ion chromatograph (TIC) or base peak plot (most intense ion plotted), or the intensity could be UV absorption or UV fluorescence, or come from other optical wavelengths, or electrochemical signal, etc.

The apparatuses and methods described herein provide improved methods and systems for analyzing data, and particularly mass spectrometry data, especially to detect and identify peaks (e.g., peptide components).

The mass spectrometry data may be acquired according to conventional methods, which typically consist of i) subjecting the sample to a separation technique, ii) acquiring an MS1 spectrum, iii) successively selecting each precursor ion observed with an intense signal on the MS1 spectrum, iv) successively fragmenting each precursor ion and acquiring its MS2 spectrum, v) interrogating databases through software (i.e. perform a computational search of observed spectra with respect to a database or a library of recorded spectra) to identify one or more molecules having a strong probability of matching the MS2 spectrum observed. In a preferred implementation, the sample is a protein that is first digested using a suitable enzyme to obtain a peptide mixture. Suitable enzymes include, but are not limited to trypsin, endoproteinase Asp-N, endoproteinase Glu-C, and thermolysin. If a protein sample contains wildtype protein and variant protein, the resulting peptide mixture will comprise wildtype peptide and variant peptide. Separation methods suitable for use in conjunction with the methods disclosed herein include, but are not limited to liquid chromatography (LC), gas chromatography, ion mobility, gel electrophoresis and capillary electrophoresis.

More than one type of digestion enzyme may be examined at once, and each may include multiple LC-MS/MS data acquisitions and multiple MS2 searches from any data acquisition. The MS2 data set may be generated using any fragmentation method, including any combination of low-energy CID, beam-type CID, and/or ETD. The quantification of a variant relative to wildtype (WT) or a similarly modified peptide is performed by label-free quantification with extracted ion chromatograms (XICs), which, in some implementations, have editable limits of integration.

Typically, the MS data is collected by a tandem mass spectrometer. In other implementations, the MS data is collected as MS1 data prior to fragmentation on a first mass spectrometer and MS2 data after fragmentation on a second mass spectrometer. In some variations, the MS data may be collected by MS1 acquisition without additional MS2 acquisition. In any of these variations, the methods and apparatuses may use an in silico prediction of candidates for identification/annotation.

The data file(s) containing the MS1 and MS2 spectra can be loaded from a storage medium or received directly from another device (e.g. over a wired or wireless connection). The spectral data may be in any suitable format. In some implementations, the data is in a format proprietary to the manufacturer of the acquiring mass spectrometer, e.g. a .RAW file for a Thermo Fisher Scientific Orbitrap spectrometer. Alternatively, the data is stored or transferred in an open format, such as mzML. For implementations comparing variant and wildtype spectra, the wild type and variant data can be obtained from a single data file or from separate wildtype and variant data files.

The list of molecular identifications can be populated from results of a computational search of observed spectra with respect to a database or library of recorded spectra. Optionally, the system described herein will accept a file containing results of an MS2 search based upon the input MS data. The MS2 search can be performed by software such as Byonic, Mascot, SEQUEST, PEAKS DB, X!Tandem, and the like. Preferably, the search software is capable of identifying variants and modifications. For example, a very common search performed by the Mascot software, and that would be appropriate as input for the methods described herein, is the "Error-Tolerant Search".

In addition to the spectral representations, the method and systems described herein may provide a description of a reference molecule. In the case of a protein, the description may be an amino acid sequence for the protein of interest in the sample. One or more chemical formulae, amino acid sequences, and/or oligonucleotide sequences can be entered manually, loaded from a storage medium or received directly from another device (e.g. over wired or wireless connection).

As mentioned, the methods and apparatuses described herein may generally be used to allow manual or automatic annotation of analytic chemical data (e.g., mapping/identification of peaks) using one or more sources of candidates. The candidates that may be used to annotate the data may be determined experimentally, by modeling, and may be provided automatically or manually. For example, in some variations candidates for annotation may be provided by an MS2 search. In other variations an in silico digest of the target molecule may be used in addition or instead of an MS2 search. An in silico digest may include modifications and miscleavages. Candidates may be manual entered or loaded from a storage medium. In the case where an in silico digest is used to generate targets rather than MS2 data, the MS2 data does not have to be recorded, just MS1 (raw) data.

EXAMPLE

In a first example, a monoclonal antibody (biologic protein) was analyzed. The intended amino acid sequence was known which results in an associated FASTA file. The sample was first reduced, alkylated, and digested with trypsin. A 3 hour LC MS/MS run on a Thermo Scientific, Orbitrap Elite™ Hybrid Ion Trap-Orbitrap Mass Spectrometer (with a CID ion trap for MS2). This resulted in a large raw data file (.raw). A UV trace associated with MS run (.CSV file of time-intensity data pairs) is also used. In this example, because the target protein sequence is known, an in silico digest list of expected peptides may be generated, which may be used with the acquired MS2 data to annotate the peptide map.

FIG. 1 is a schematic overview of one variation of a method for creating and annotating (including automatically annotating) a peptide map as described herein.

Following preparation of a sample including the target molecule (e.g., protein(s)), and mass spectroscopy (MS), candidate peptides may first be identified from the sample data using a candidate search (e.g., MS2 search) based of the raw MS data and the FASTA data. Any appropriate search may be performed; see, e.g., U.S. patent application Ser. No. 14/306,020, filed on Jun. 16, 2014 ("INTERACTIVE ANALYSIS OF MASS SPECTROMETRY DATA"), describing methods, including software, for performing candidate searching (e.g., using a tool such as Byonic™ from Protein Metrics, Inc.). The search results may then be used with the raw mass spec data including the UV data to form an annotated (automatically annotated) peptide map.

The methods of analyzing (e.g., generating a peptide map and/or annotating a peptide map) may include accessing the original MS data, the candidate peptides identified from the candidate search, as well as any additional identified or putative candidates, such as in silico predicted candidates. The resulting data may be used to generate a peptide map, which may be modified and annotated as described herein, including automatically annotating the peptide map. In some variations the same methods and techniques identified herein to identify and/or annotate the peptide map may be used to quantitatively compare files, including filed representing different samples and/or different experimental runs of the same sample.

Automatic annotation (and in some variations manual annotation) may include applying threshold values, which may be user-adjusted or defined, to set the accuracy threshold for selecting between candidates for annotation. For example, MS1 accuracy may be used to make (e.g., automatic) associations between candidates and observed masses within a chromatograph peak time window. The accuracy threshold of acceptability and intensity threshold (s) may be set (defined) by the user. When automatically annotating, the apparatus and methods may apply the threshold to so that candidates outside of the target range (e.g., within 10 ppm) are not annotated with the peak, while candidates within (e.g., less than or equal to) the threshold range are annotated.

For example, the candidates identified by searching, as well as the appropriate mass spec file used for the search identifying the candidates may be used along with a UV trace associated with the raw data may be used. The method, or an apparatus configured to perform the method, may be used to identify peaks either or both the UV trace or the MS file, and these peaks may be identified and/or annotated using the candidate information from the search and any other information, such as the in silico prediction of candidates and the FASTA data. For example, the system may perform the method of using a UV file associating and aligning traces on the UV file with traces in the MS data file.

Before, during or after the analysis, the apparatuses and methods described herein may modify the data to enhance the analysis. For example, the apparatus or method may adjust the baseline, and/or allow the user select portion of interest. For example, if (as is usual) the user knows when/where in the data the peptides of interest dilute, the apparatus or method may allow the user to designate the relevant elution time range (e.g., from 6 to 165 minutes).

The FASTA information may be used to assist in mapping as well, listing putative peptide sequences. The target protein (peptide listing) may also be specified and used for the analysis. In the example illustrated above, in which the target sequence is a particular monoclonal antibody, the user may select all or a portion of the protein to analyze, such as either or both the heavy and light chains (and exclude non-target proteins, such as trypsin, which may be part of the sample).

As mentioned, the data files may be processed to determine and/or modify an initial base line and peak determination. The user may review and make adjustments using the tools described herein, including time correlation between two or more data sets (including UV and/or MS data), non-linear time alignment (e.g., warping), peak detection, selection and/or modification, and automatic assessment of candidates (e.g., base on m/z accuracy).

Figure 2:
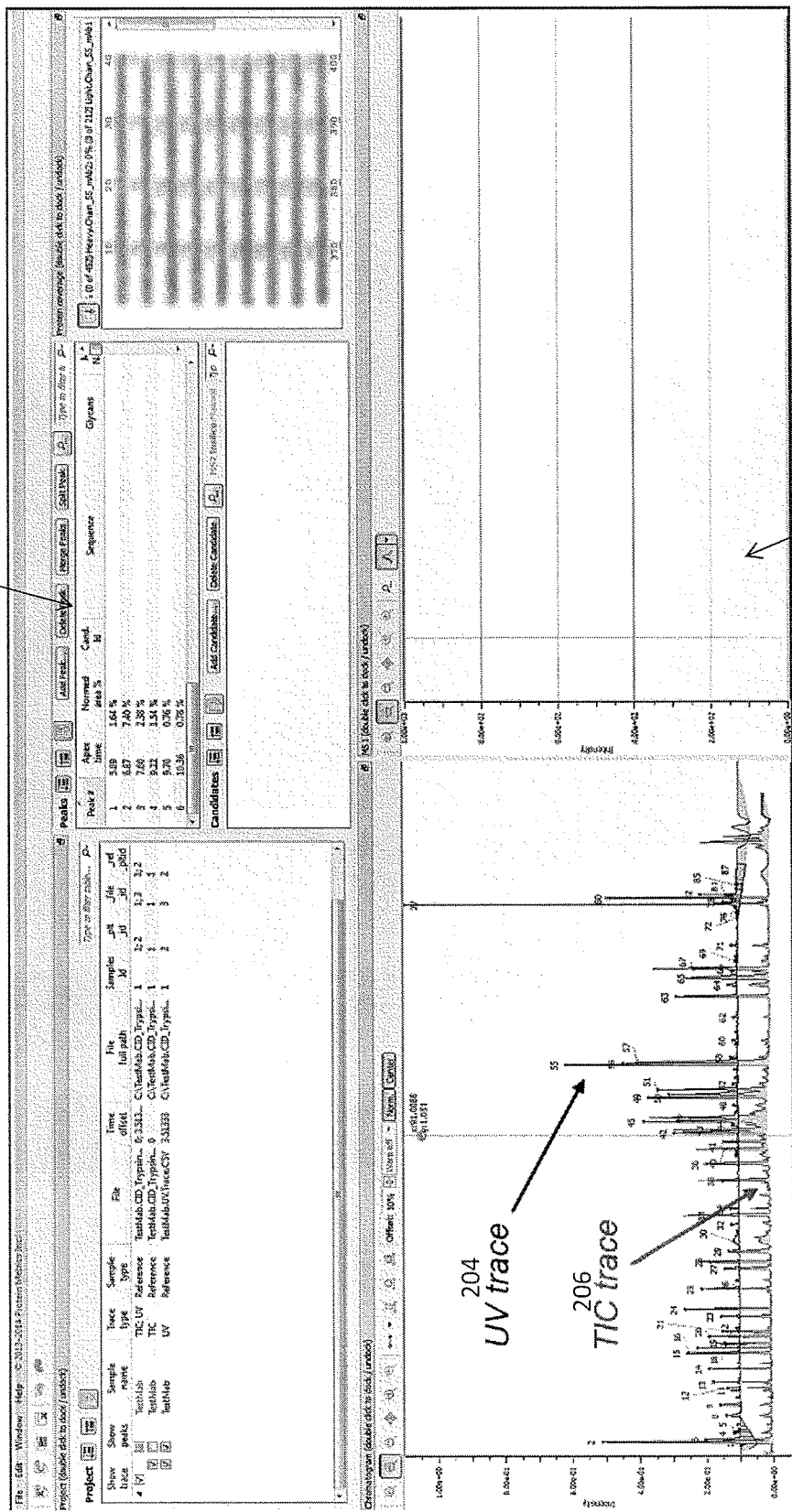
FIG. 2 is one example of a user interface including various windows for displaying mass spectroscopy (MS) data and corresponding chromatographic and annotation data.
Figure 3A:
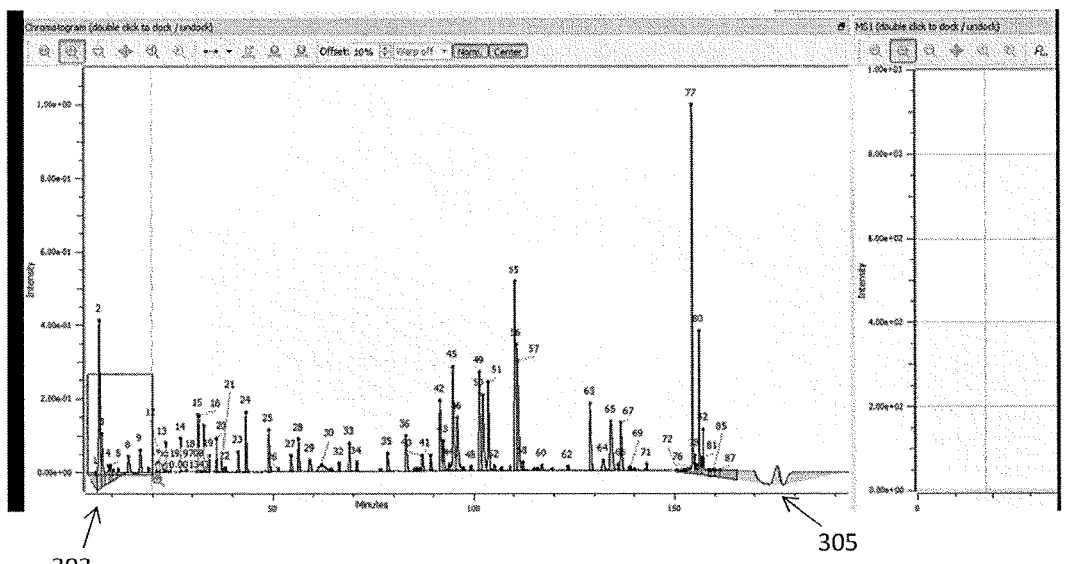
FIGS. 3A-3E illustrate the baseline adjustment of a chromatograph (UV data).
Figure 3B:
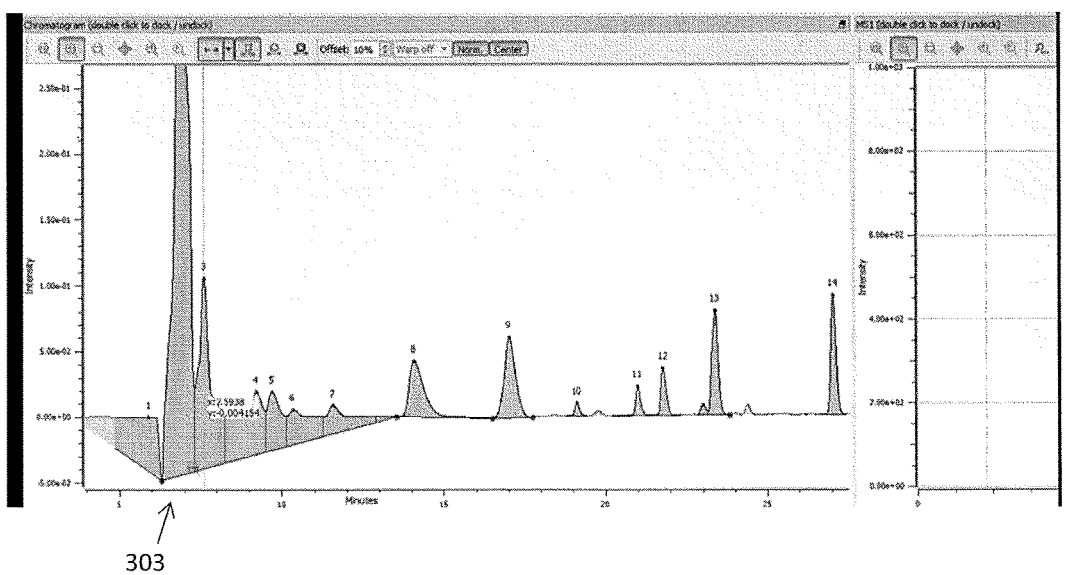
Figure 3C:
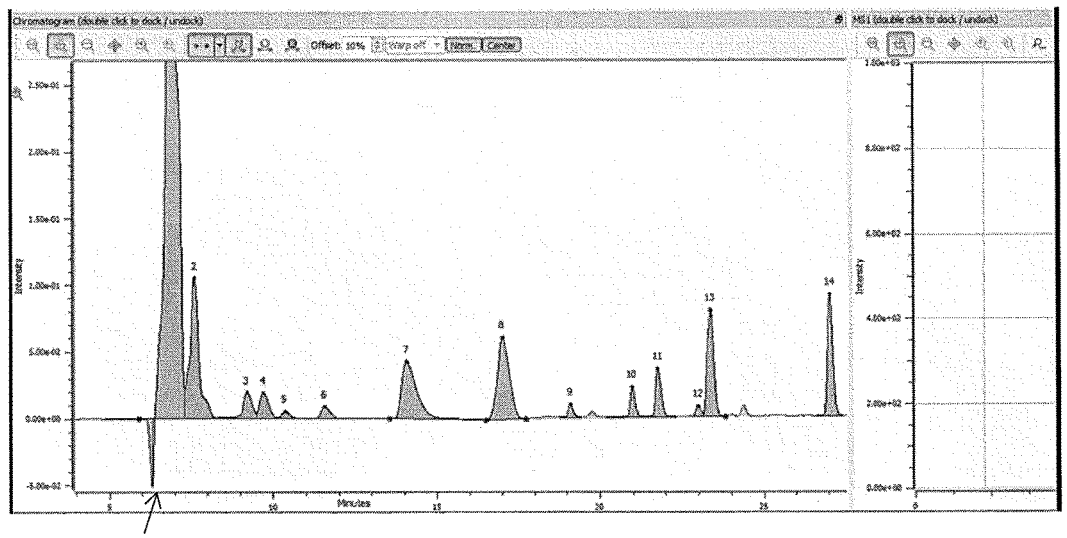
Figure 3D:
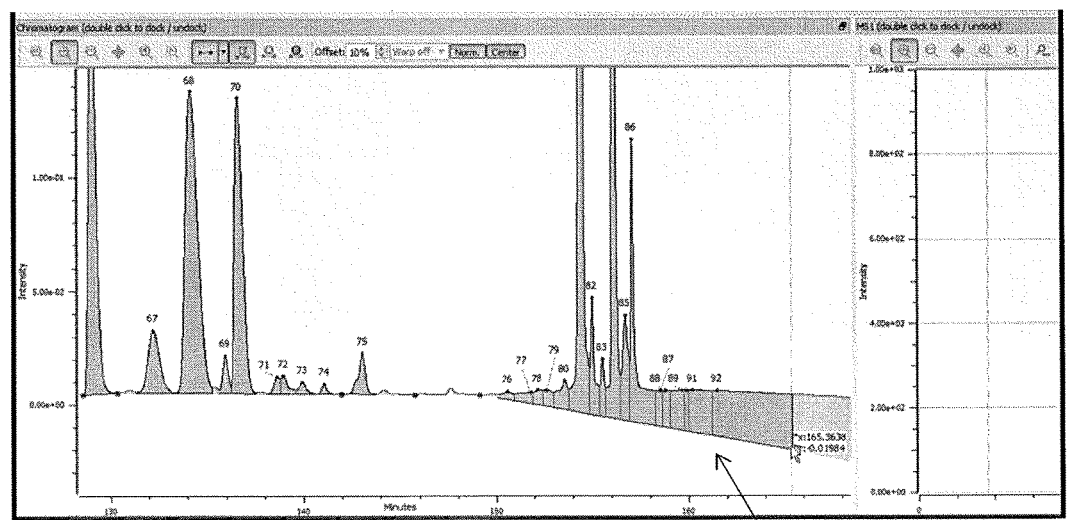
Figure 3E:
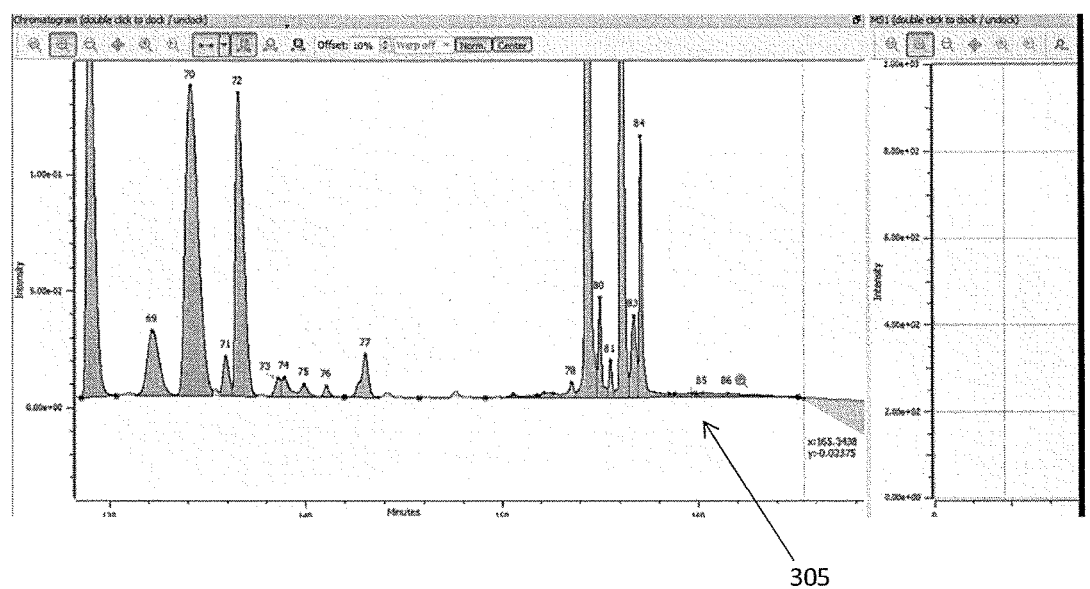

Any of the apparatuses described herein may include an interface that may operate as an additional tool or an accessory portion of the tool for analyzing the data. For example, the screen or display may be arranged to include numerous windows simultaneously displaying multiple classes of information; these windows may be manipulated and changes made in one of the windows may be reflected in the other windows as well. In general, these windows ("views") may be interactive, allowing the user to make changes (including annotations, etc.) onto the displayed data. The apparatus may also store (in an ongoing manner, so that separate storing commands are not necessary) the generated information, correlation and user modifications. As mentioned, the views may show the data, as well as information about the data, including the type of data, the origin of the data, etc. For example, the name of the sample may be shown in a project window at the top left as well as a trace type, the file name and path, and the time and scan number metadata. The user may toggle between the data or between windows/views (e.g., showing TIC and UV traces, etc.). For example, as shown in the example in FIG. 2, a chromatogram window 202 is shown in the bottom left of the screen, allowing the user to annotate either the UV trace 204 or the TIC trace 206 or both. In this example, the windows may include tools for modifying/annotating the data shown. For example, a chromatogram window 202 may provide additional tools that allow the user to manually adjust and refine the base line. In particular, a UV base may be non-flat, particularly towards the beginning 303 and end 305 of the elution data, as shown in FIG. 3A. The user can point a cursor on the base line and move it to adjust (flatten) the baseline manually (see, e.g., FIGS. 3B-3E); alternatively, this may be done automatically and turned on/off or adjusted. The user may also review the data to identify or confirm peaks identified by the apparatus/method, as described in more detail below.

Figure 4:
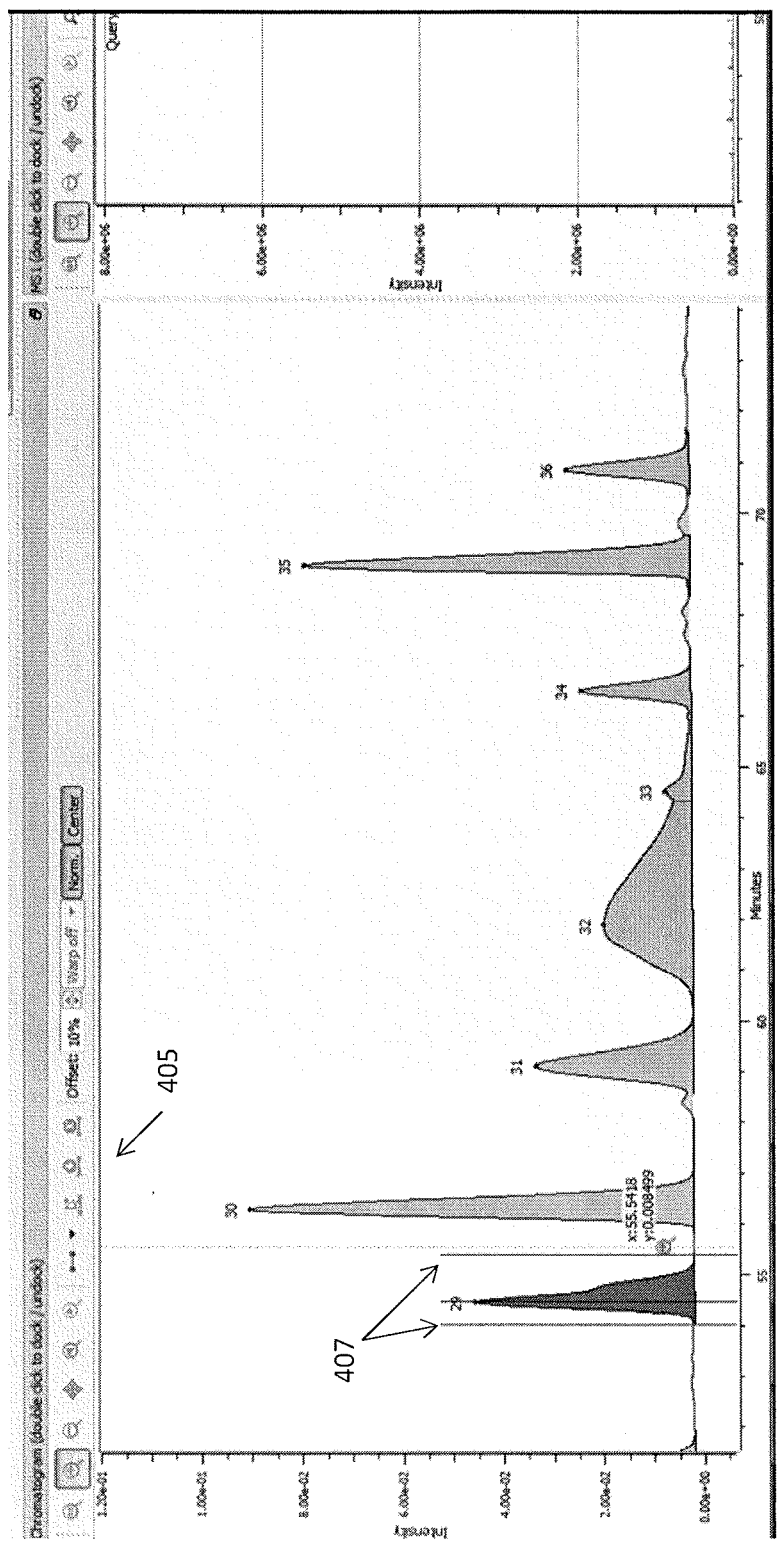
FIG. 4 is an example of an enlarged view of a UV chromatogram.
Figure 5:
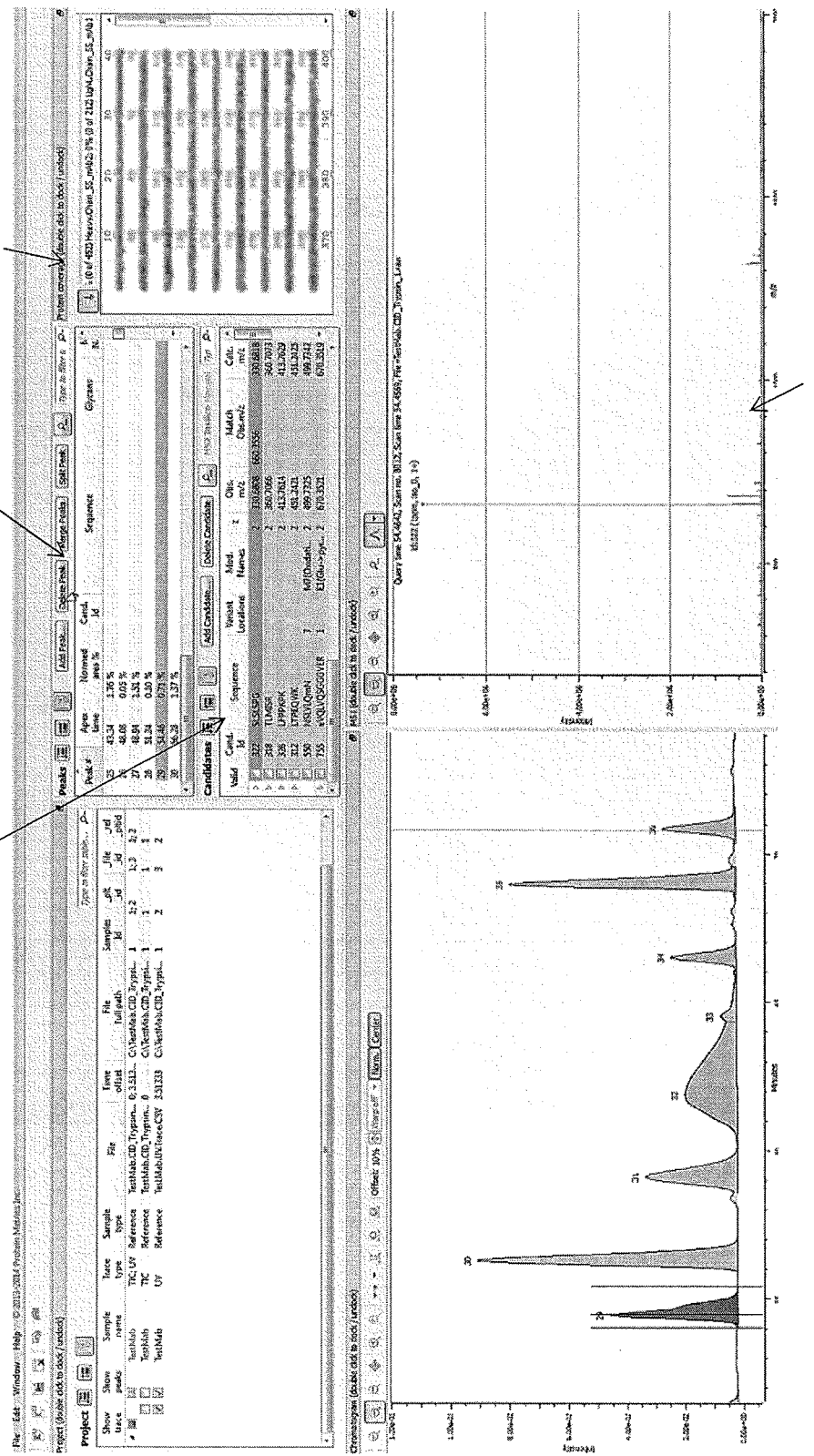
FIGS. 5 and 6 show examples of a user interface (UI) showing different window regions concurrently displaying information relative to annotation of the peptide map, including a peaks window, a chromatogram window, an MS1 window, a protein coverage window, and a candidates window.
Figure 6:
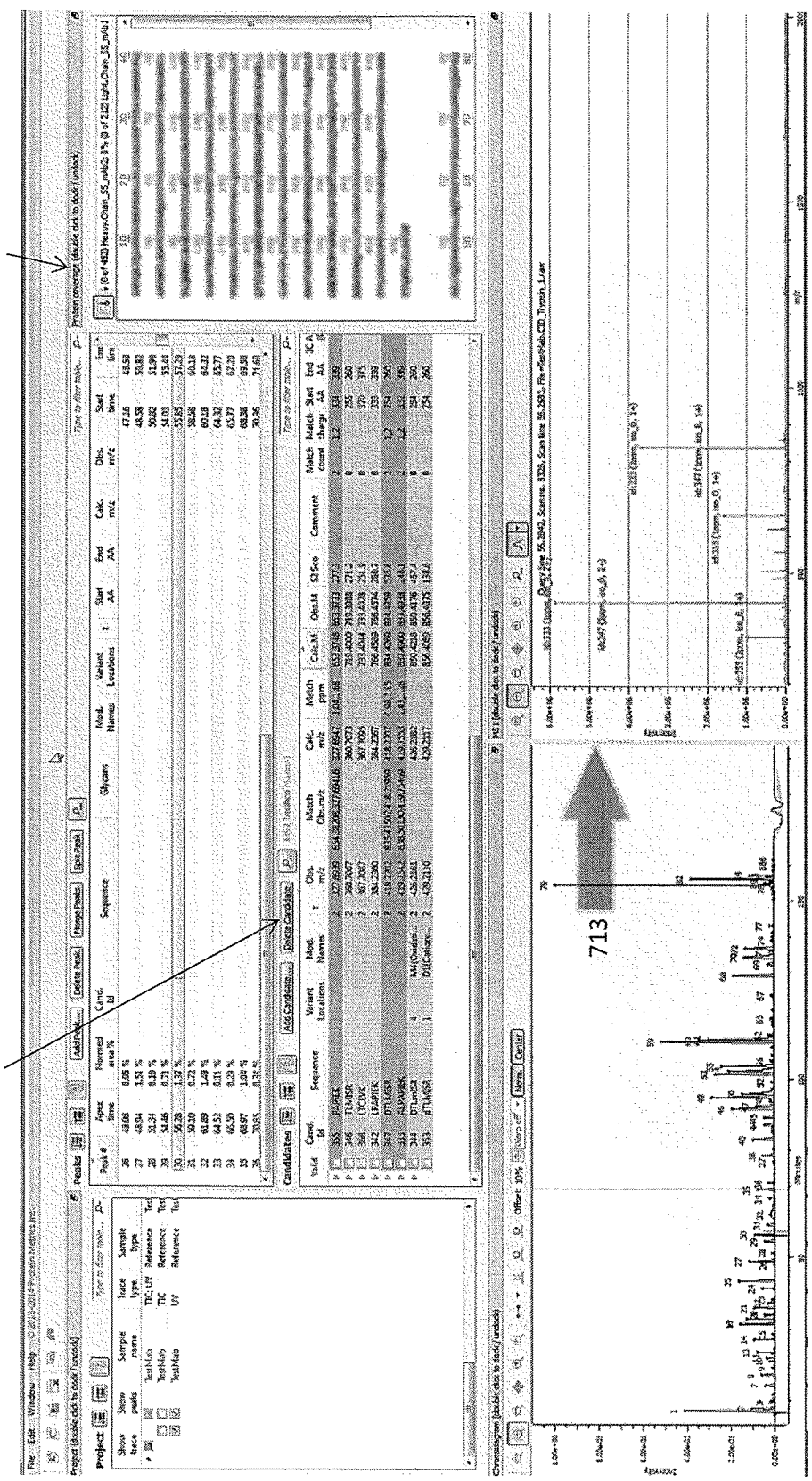
Figure 7A:
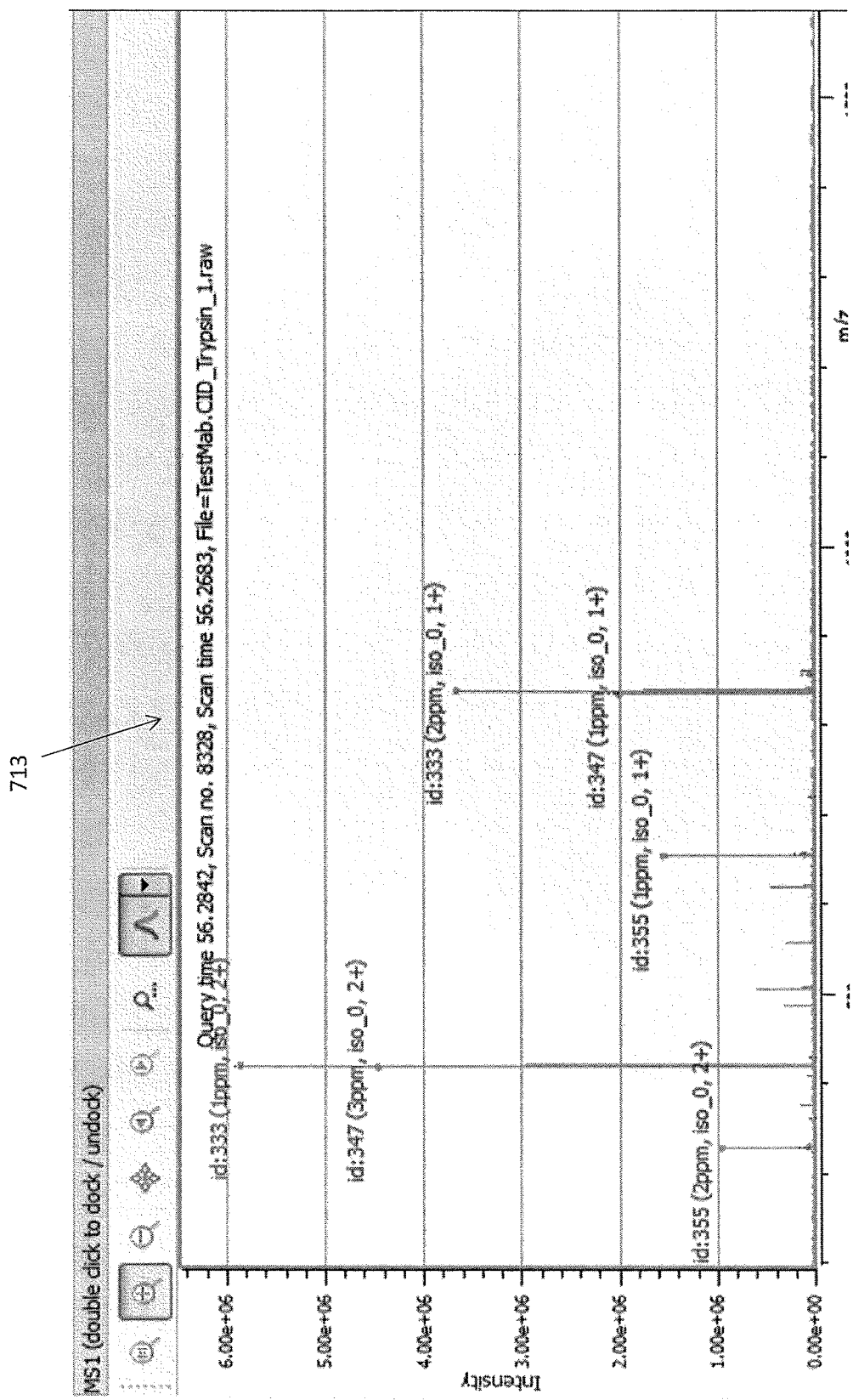
FIG. 7A is an enlarged view of the MS1 window showing MS data for a particular time (which may correspond to the cursor position on the chromatogram).
Figure 8:
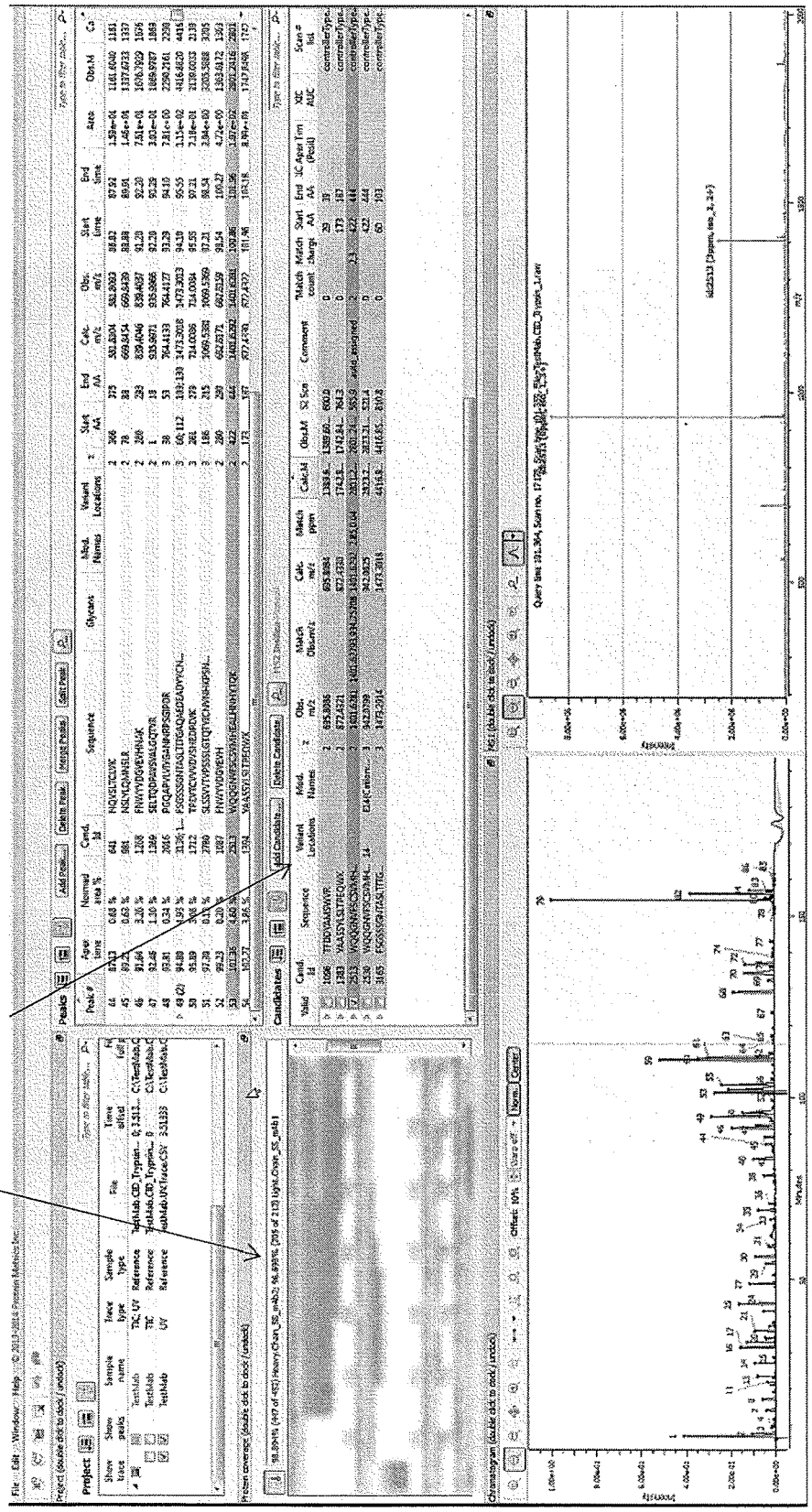
FIGS. 8 and 9 are examples of user interfaces after the apparatus has automatically annotated a trace.

For example, a user may add, remove, or adjust the peaks identified and used for analysis. For example, the user may vary the bounds of integration for any peak, and may also split or merge peaks. An example is illustrated in FIG. 4, which shows one example of a chromatogram window allowing a user to modify the bounds of a peak (shown in vertical lines 407 around one peak) by selecting tools from the tool bar 405. Even when peaks are automatically identified, the apparatus and method may allow the user to refine the peaks selection. Peaks may be annotated in one or more window, including non-graphical (e.g., text, alphanumeric, etc.) displays such as a listing of the identified peaks that may be annotated as well. In the example shown in FIG. 4, the peaks are numbered (29-36). For example, selecting a peak may highlight the corresponding row in a "peaks" window 509 (e.g., at the center top of the user interface in FIG. 2 and FIG. 5). The user interface may concurrently display a corresponding MS1 plot in a MS1 window 713 (e.g., at the bottom right in FIGS. 2, 5 and 6). FIG. 7A shows the MS1 window in greater detail. Columns in any of the display windows (e.g., in the "peaks window" 509) may list data such as like peak retention time, peak area, the sequence, modification, the mass, charge data, etc. that may be derived from the annotation assignment. The user interface may also include a view (e.g., "candidates window") listing putative candidates for the peaks that have been identified from the putative (e.g., MS2 predictions, in silico data, etc.). In FIGS. 5, 6 and 8, a candidates window 511 is shown in the center below the peaks window 509, and a protein coverage window 519 is shown at the top right in FIGS. 5 and 6 and middle left in FIG. 8 (also illustrating how the user may customize the display to move the windows into different positions and re-size them as desired). A protein coverage view 519 (window) may be used to identify the extent of coverage identified (and annotated) for the target protein as the protein map is annotated. Annotation may confirm the putative identification of peaks that may be provided by the candidate search and/or in silico predictions.

Figure 7B:
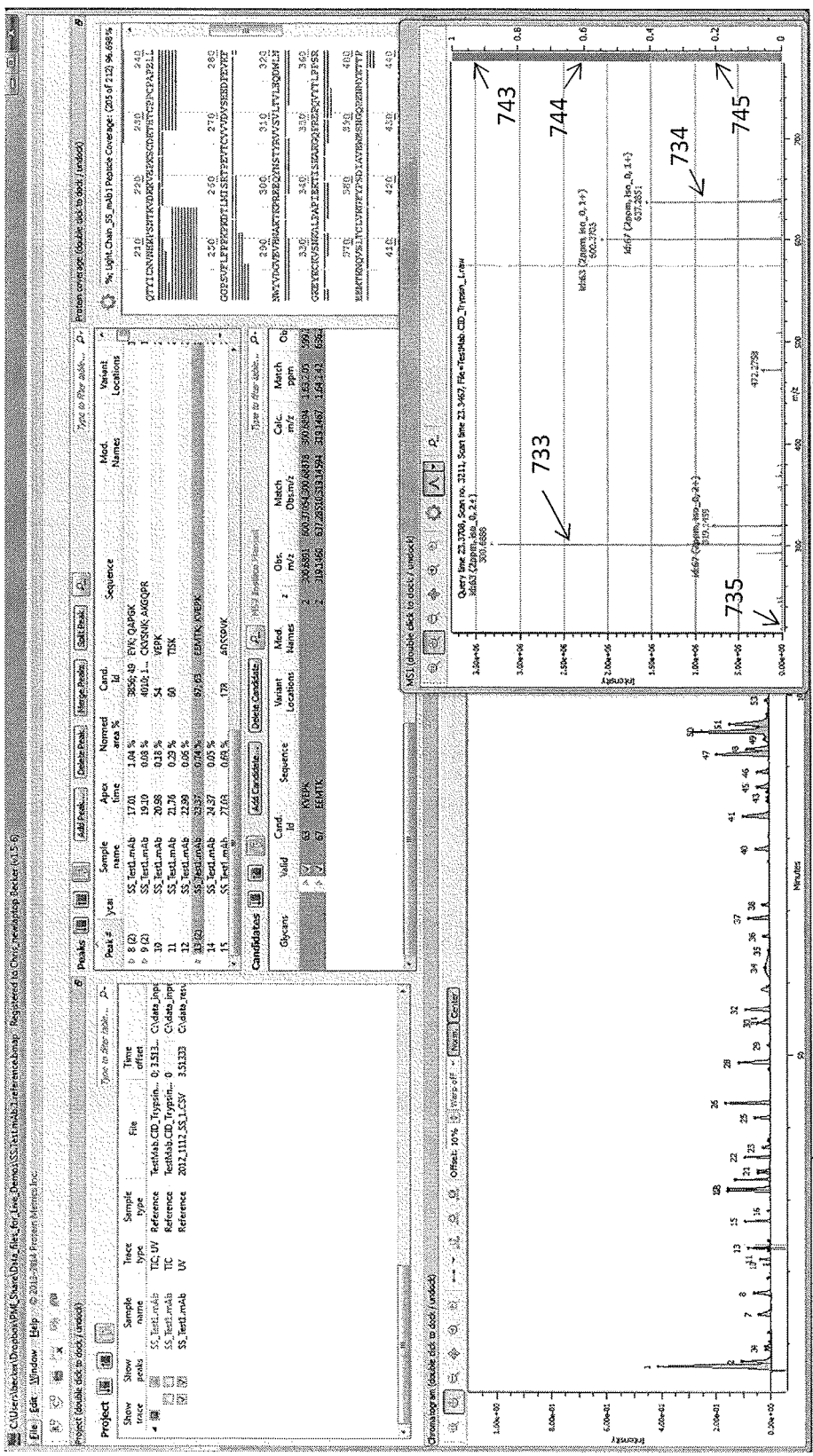
FIG. 7B is shows an example of a UI including a window at the bottom right showing an m/z plot that may be color-marked (e.g., green, magenta, and gray) to indicate correlation ranges, and may also be labeled with exposed correlation coefficients. The scale bar on the right illustrates the ranges of the graded correlation coefficients.

FIG. 7B shows another example of a user interface (UI) including an MS1 window 723 corresponding to the time point indicated in the chromatogram window 766 in the lower left of the UI. The MS1 window shows the mass/charge data at that time and includes peaks that marked (e.g., in this example by both color, e.g., green 733, magenta 734, and gray 735, and alphanumeric text) to indicate correlation. The correlation ranges corresponding to the color coding (and generally to the ranking) may be shown in a scale bar; in FIG. 7B, the scale bar showing ranging (low in grey 745, medium in magenta 744, and high in green 743) is located on the right.

In general, the apparatus may allow any of the views (windows) to be resized, popped out, or rearranged for personalized viewing. When the user is using the apparatus, it may store information as the user is operating the apparatus, constantly updating a local database. Thus, all changes may be captured in real time and saved to the database so that no data is lost.

As mentioned above, peaks may be identified and tentatively annotated by making assignments either automatically, manually, or combination of the manual and automatic. For example, to make assignments, candidates may be taken from the provided MS2 search, in silico digest list, etc. Additional candidates may be imported as well (e.g., from other, previously run analyses, etc.). The apparatus may display the different candidates with marking to indicate their origin (e.g., marking in silico candidates in different colors and/or fonts and/or locations than those identified by MS2 search, etc.). It may be particularly helpful to display similar candidates from different sources (e.g., MS2 search data and in silico data) corresponding to present likely peptide matches next to each other, allowing the user to visually confirm. With candidates loaded, the candidates window may be populated with potential assignments for any selected peak that matches a corresponding search candidate spectrum (e.g., MS1/MS2/MS3). The apparatus may also annotate the MS1 window with those assignments.

As mentioned above, a user can manually step through the peaks and review the various candidates to validate annotations. Validated peptide information may be displayed; for example validated information (annotations) may be displayed in the fields in the peaks table and the sequence is marked in a protein coverage map. This process may be relatively quick and straightforward. However, given the large number of peaks that could be examined, the apparatus may also or alternatively annotate automatically. When automatically determining candidates, the apparatus may compare a theoretical isotope distribution to experimental MS1 data.

Figure 9:
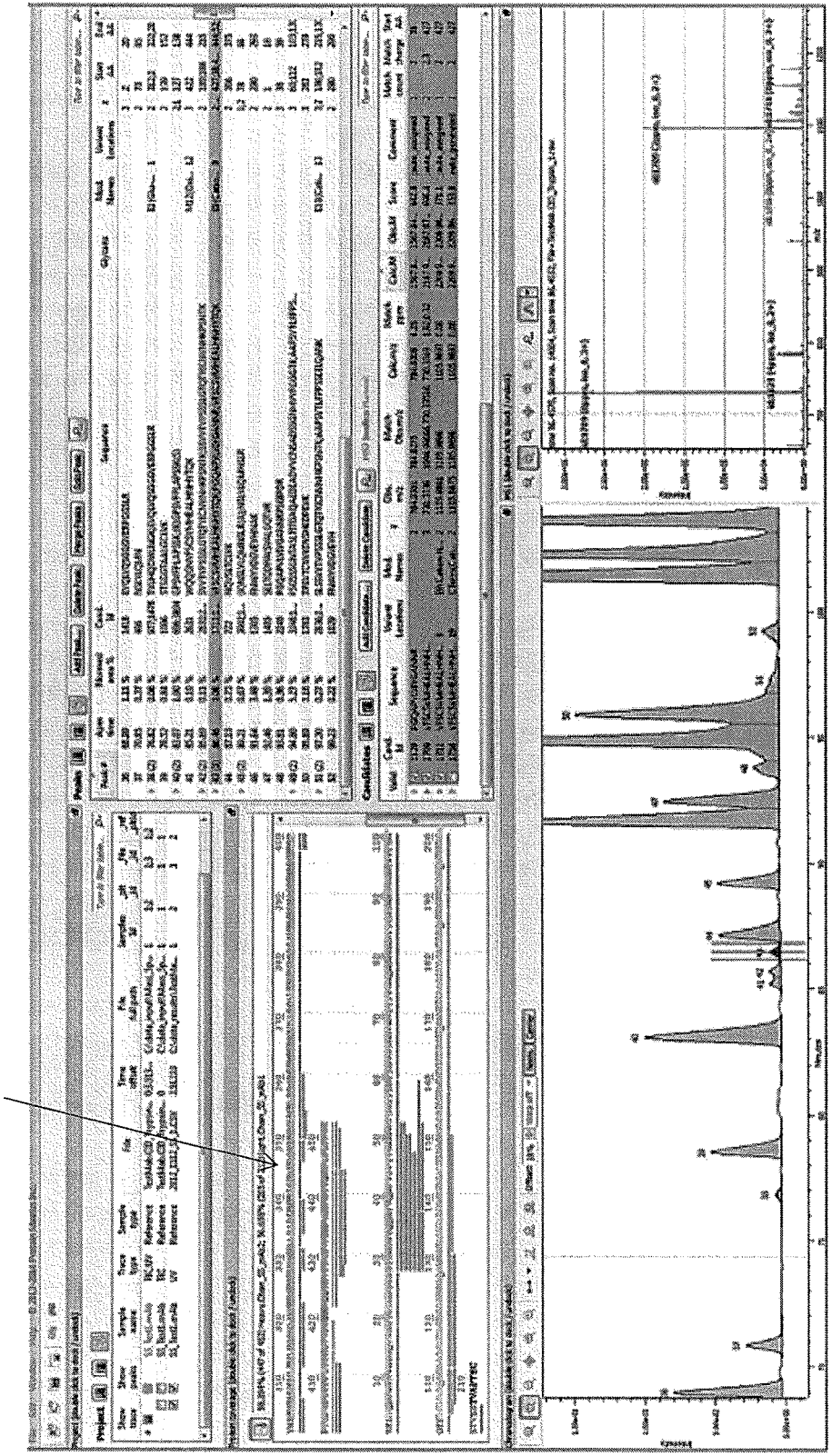

In FIGS. 8 and 9, automatic annotation fills in 99% of the heavy chain and 97% of the light chain in the earlier mAb example, as schematically illustrated in the protein coverage window 519. Following automatic annotation, the user may still go through and verify individual identifications, and (when satisfied with the assignments) may export the results and create a report.

In some variations the apparatus allows a user to customize the arrangement of the peaks table and then export the table to create a report. The format, and the resulting data, may be stored, printed, etc., and may be saved and/or transmitted, including exporting to other systems. Reports may include graphical and textual data, including information showing annotated peptide maps that include metadata and information about the sequence and the digestion. Chromatogram figures may also be included in the report as well. For example, a report may be generated to include identified peaks, including those predicted from in silico digest, as well as all the relevant annotations, assignments, quantifications, and associated details. The apparatus (including the output report) may also summarize any peaks that were not annotated. In general, the apparatus may export a single chromatogram of interest matching any of the views presented. In addition, series of zoomed images may be exported.

As briefly described above, the apparatuses and methods described may display MS data from different data sets, including from different detectors and different modes (e.g., UV and MS), and the data may be peptide mapped together to allow immediate comparison. In addition to the tools and functionality described above, the apparatuses and methods may allow signals to be aligned (including non-linear time alignment) and time correlated by interacting with visualization of MS spectra at different times.

For example, after importing one or more MS data files showing the detected ion chromatogram (and corresponding HPLC UV traces), the traces may be aligned and annotated to form the peptide map. In forming an annotated map, each peak may be identified (as described above, either automatically and/or manually) and labeled. The labeling/identification is persistent and correlates information with the identified peak so that it is concurrently displayed in different windows and can be traced to different reports. For example, candidate information (displayed concurrently in a candidate window) may be linked, by annotating, to a particular peak.

Alignment

As mentioned, when a display window shows multiple traces (e.g., both TIC and UV traces; multiple TIC and/or UV traces, etc.), the different traces may be aligned. In some variations it may be particularly advantageous to "warp" the traces for display, so that they may be visually aligned by remapping them to allow them to be visually inspected by the user, who may make decisions about the traces based on the "warped" display. Thus, the "warped" alignment techniques (and apparatuses configured to generate and display them) described herein may be helpful in forming the annotated peptide maps and comparisons described.

In general, when displaying multiple chromatographic traces (e.g., UV, TIC, etc.) and aligning them, all of the traces may be aligned relative to another, "reference" trace. Apparatuses and methods of displaying a plurality of traces (e.g., chromatographic traces) may allow visual inspection of the traces by comparing signals intensities between different chromatographic traces relative to a reference chromatographic trace. For example, to perform a warping alignment of one or more chromatographic traces to align them with a reference chromatographic trace, an apparatus may first generate a time transformed trace of a first chromatographic trace by comparing signal intensities from the first chromatographic trace with signal intensities of a reference chromatographic trace and adjusting the time values from the first chromatographic trace to correspond to time values of similar signal intensities of the reference chromatographic trace. This adjustment of the time values form an initial alignment, but alone is not sufficient. The apparatus may then identify a plurality of reference "anchor points" from the reference chromatographic trace; reference anchor points are typically points of peak signal intensity (maximum). These points may be identified automatically, in which case they may be determined by identifying local or regional maxima (e.g., indicating peak and peak separation regions), or they may be manually set by the user (and do not necessarily correspond to a maximum). Thereafter, the apparatus may determine a corresponding anchor point in the first (non-reference) chromatographic trace for each of the reference anchor points from the first time transformed trace. These correlated points may then be used to generate a second transformed chromatographic trace from the time values for each of the corresponding anchor points by (e.g., linearly scaling time values from the first chromatographic trace between time-adjacent pairs of corresponding anchor points. The resulting scaled and shifted ("warped") transformed first chromatographic trace may be displayed by the apparatus and will be aligned with the reference chromatographic trace. The same process may be repeated (against the same reference trace) with as many additional traces are to be co-displayed with the reference trace.

In performing this method, the apparatus may divide the first chromatographic trace and the reference chromatographic trace into a plurality of sub-regions for comparison when generating the first time transformed trace. Following the first pass in which the first time transformation is performed, identifying the plurality of anchor points may include identifying local maximum and flanking minimum intensity values from the reference chromatographic trace forming a peak in the reference chromatographic trace. For example, determining the corresponding anchor point may comprise using the first transformed first chromatographic trace as a map to identify the corresponding anchor points in the first chromatographic trace.

Once the non-reference traces have been transformed so that they can be aligned for visual co-inspection, they may be presented adjacent to each other. For example, displaying may include presenting the second transformed first chromatographic trace immediately above or below the reference chromatographic trace. Displaying may include presenting the second transformed first chromatographic trace on top of the reference chromatographic trace. As mentioned above, the display may also include presenting the different traces in different colors.

Although the display and user's visual inspection may benefit from the warping display techniques described herein, the analysis (including automated peak analysis, etc.) performed by the apparatus may be done in non-warped space even when the traces are displayed in "warp space."

As just described, the overall process of transforming a trace relative to a reference trace for alignment by warping may be considered a two-part process. In the first part, the trace(s) maybe segmented into numerous small segments. Each segment may then be scaled to optimize the comparison between the non-reference trace ("first chromatographic trace") and the reference trace ("reference chromatographic trace"). This first part is a highly granular mapping of the time points to generate a mapping, point by point, between the target (reference) and a non-reference traces. This may be considered a dynamic time warping. Further, although this first pass is quite precise in transforming of the non-target trace, it is not sufficient, and does not provide a transformation that can be used directly to map/display the aligned traces, because it results in an image that is too skewed. When displayed, the transformed trace(s) do not appear as desired (e.g., in particular, peaks are incorrectly shaped). The first part may also be referred to as part of a dynamic programming method, or a dynamic warping method.

Thus, a second pass may be performed on the first transformed trace to further warp the trace while providing a particularly meaningful and useful display for purposes of alignment and between-trace comparison. As discussed above, in the second pass, the apparatus may examine the reference trace to determine anchor positions (in a procedure that may be referred to as a critical point finder). When performed manually, the user may indicated points (e.g., on the reference trace) with which to anchor the comparison. Alternatively or additionally, automatic analysis of the reference trace may be performed to identify anchor positions based on the peaks (including in particular regions around the peaks). Both manual and automatic determinations of anchor points may be made. Once the critical points are identified from the reference trace, the critical points may be identified in the non-reference trace that was transformed in the first part. Then the apparatus may use the critical points (anchor points) to map the non-reference trace to the reference trace, so that there is a one-to-one mapping of these points; the regions between these points may then be linearly transformed (e.g., just between the matched anchor points).

Figure 10A:
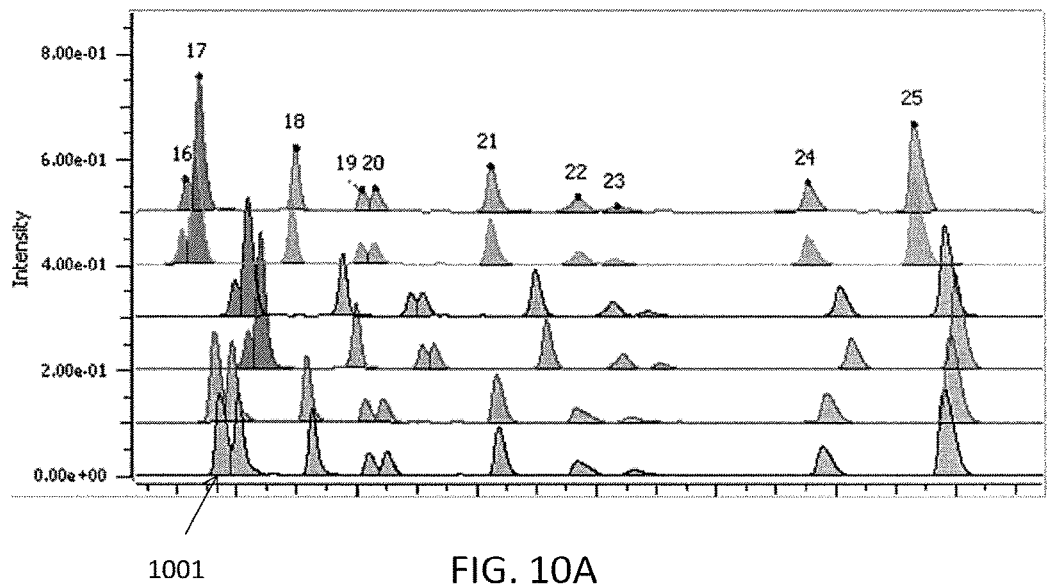
FIGS. 10A and 10B illustrate warping (alignment) of multiple traces to a reference trace (chromatogram traces).
Figure 10B:
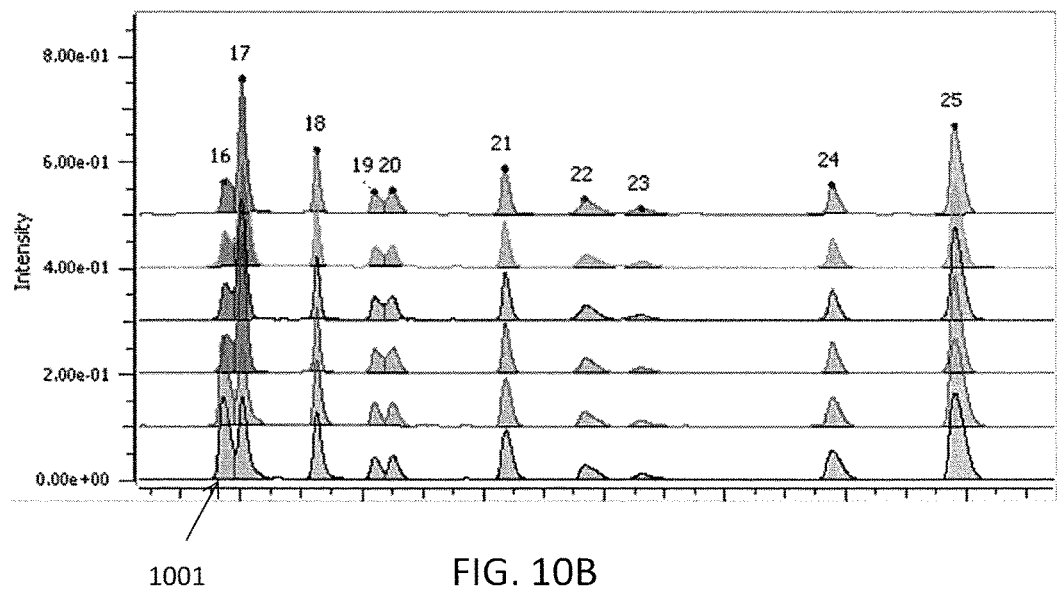

FIGS. 10A and 10B illustrate an example of time alignment (warping alignment) as descried. In this example, in FIG. 10A, the bottom trace 1001 is used as the reference trace, and the five traces above it are to be aligned with the reference trace. For each trace, the two-part alignment (warping) method described above may be used to transform the traces so that they can be meaningfully aligned for side-by-side comparison, as shown in FIG. 10B. The two-part alignment technique described above allows the peaks to be easily compared at numerous magnifications, so that the user may readily compare them.

When performing the warping alignment as described, any appropriate trace (e.g., MS or TIC, UV, etc.) may be used. Other trace types include HPLC, CIEF, capillary electrophoresis, etc.

Time Correlation

The apparatuses and methods described herein may also perform time correlation of MS data and corresponding chromatographic data when annotating a reference trace (e.g., a reference peptide map). For example, time-peak information may be correlated from a chromatogram (e.g., TIC, UV, etc.) trace with mass spectrogram (MS intensity) data. When time correlation information is used to annotate or otherwise label a peak (or peaks) in the mass spectrogram, this may enhance the user's understanding of the nature of the peak.

Thus, time correlation may provide an additional method of displaying a correlation between a candidate molecule (e.g., peptide) and a candidate chromatographic peak. As an overview, time correlation may be used to examine a peak from a chromatograph that is present over a time (x-axis is time). This same time period may be examined in the MS1 data, to look at intensities at one or more regions (segments) in of mass/charge (e.g., where the x-axis is the MS1 plot at a given time point is mass/charge). By examining the time course of the intensity of one or more mass/charge segments from the MS1 plat over the time in which the peak in the chromatogram is occurring, and in particular, by comparing the relative rate of change in the intensity of the chromatograph peak to the rate of change of the intensity of one or more segments of mass/charge from the corresponding MS1 plot, a score or value may be determined and used to interpret (and/or label) the peak. The resulting score may reflect how closely associated the peak is with a particular molecule (e.g., peptide) or family of molecules (e.g., isotopes).

An apparatus performing time correlation may use peaks from a chromatograph in reference to an associated raw MS data (e.g., MS1 trace). For example, the apparatus may first determine or define a timer period from the chromatograph that corresponds to a region of the peak signal intensity. The time period may include primarily the peak region (e.g., the maximum and a narrow or broader region surrounding the maximum). Alternatively any window of time within the peak may be used. In some variations the window is a fixed duration; in some variations the window is set by a user manually. The window may also be set automatically, e.g., based on the steepness (rate of change) of the intensity value of the peak within the window. Once the time period has been determined, the apparatus may examine the corresponding MS1 (mass/charge) intensity values from the MS data during this time period. The apparatus may first divide the mass/charge axis (the x-axis of the MS1 data, for example) into segments/sub-regions. The size of the segments may be predetermined or may be modified by the user.

For at least one segment, the change in the intensity values at that mass/charge segment may be determined over the time period chosen from the chromatograph. In some variations, the mass/charge segment having the greatest intensity may be used; in other variations, the mass/charge segment having the greatest average charge over the duration chosen may be used.

Thereafter, the time course of the intensity ("relatively intensity") of one of the mass/charge segments over the determined time range may be compared to the time course of the signal intensity (e.g., shape of the portion of the chromatographic peak during the time range) to determine a score value or correlation coefficient. This score value may be used to label the peak (including graphically labeling the peak image and/or labeling in the Peak window described above). Thus, if the change in the intensity (relative intensity) values of a mass/charge segment (which may correspond to a particular species) is strongly correlated with the peak in the chromatograph, the resulting score may be near 1 (e.g., the change in the peak shape may be highly correlated with the changing intensity value over time for that mass/charge segment, which is therefore likely to correlate with the species responsible for at least some of the mass/charge intensity in that segment. Similarly, if the time course of the change in intensity values of a particular segment (and in some variations all of the segments may be individually examined and compared) is not well correlated with the shape of the region of the peak within the selected time range, then it is likely that the peak is not strongly (or exclusively) correlated with the species responsible for the mass/charge intensity in that segment.

Thus, time correlation may be used to help annotate the peptide map, by furthering understanding of the nature of the identified peaks. The scores resulting from the time correlation may be used to flag or otherwise indicate that the peaks should be manually or automatically adjusted (e.g., by dividing the peak into multiple peaks, etc.), or for example, that they belong to neighboring chromatographic peaks or are uncorrelated background ions.

As mentioned, in some variations a mass-charge segment is selected from all of the possible mass/charge segment in the raw (e.g., MS1) data for comparison with the peak shape during the time correlation. In some variations, all of the mass-charge segments may be examined and compared; in some variations only a subset (or a single) mass-charge segment is compared with the peak shape. For example, the method may include selecting a mass/charge segment from within a mass/charge region that has an intensity that is greater than a threshold value (e.g., greater than 1.0E7, 5E7, 1E6, etc.).

The time correlation score may be used to annotate; for example the time correlation score may be used to mark the MS1 peak (or the region of the peak within the selected time), including coloring the peak to indicate the value (or range) of the score.

Any of the apparatuses and method described herein may also include a tool for identifying or highlighting features of interest (e.g., a "feature finder"). This tool may examine the MS data to identify smaller features (e.g., between a maximum and minimum value) and export or otherwise flag them for further analysis by the user. The minimum and/or maximum peak intensities may be modified or set by the user.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for the automated analysis and annotation of a peptide map, the method comprising:
   importing candidate peptides related to a target protein;
   concurrently displaying a chromatographic trace, a listing of candidate peptides, and a mass over charge (m/z) trace;
   automatically annotating peaks of the chromatographic trace using the listing of candidate peptides; and
   displaying the annotated peaks concurrently with the chromatographic trace, the listing of candidate peptides and the m/z trace;
   receiving, from a user, a selected time period from the chromatographic trace comprising a region of peak signal intensity;
   determining intensity values at one or more m/z segment for each of a plurality of times within the selected time period;
   comparing a time course of the intensity values for the m/z segment over the time period to the time course of the chromatographic trace signal intensity over the region of peak signal intensity to determine a score of the comparison; and
   annotating the m/z trace with a visual representation of the score of the comparison.

2. The method of claim 1, further comprising concurrently displaying a plurality of additional chromatographic traces.

3. The method of claim 2, further comprising aligning the plurality of additional chromatographic traces with a reference chromatographic trace.

4. The method of claim 1, wherein automatically annotating the peaks comprises applying a user-definable threshold of the candidate peptides based on accuracy scores associated with each candidate.

5. The method of claim 1, further comprising allowing a user to manually annotate peaks of the chromatographic trace.

6. The method of claim 1, further comprising allowing the user to modify the chromatographic trace display.

7. The method of claim 1, further comprising adjusting a baseline of the chromatographic trace.

8. The method of claim 7, further comprising allowing the user to manually adjust the baseline.

9. The method of claim 1, further comprising generating a report including the annotations.

10. A method of displaying a correlation between a candidate molecule and a candidate chromatographic peak, the method comprising:
    concurrently displaying a chromatographic trace and a mass/charge (m/z) trace;
    receiving a user-selected time period from the display of the chromatographic trace that includes a region of peak signal intensity;
    determining intensity values at a m/z segment for each of a plurality of times within the time period;
    comparing a time course of the intensity values for the m/z segment over the time period to the time course of the chromatographic trace signal intensity over the region of peak signal intensity; and
    concurrently updating the m/z trace with a visual representation of an indicator of a score of the comparison.

11. The method of claim 10, further comprising selecting the m/z segment from within a mass/charge region having an intensity that is greater than a threshold.

12. The method of claim 10, further comprising selecting the m/z segment from within a m/z region having an intensity that is greater than a threshold percentage of a maximum value of the intensity within the region of m/z.

13. The method of claim 10, further comprising labeling a visual representation of the m/z segment in a mass spectrogram with an indicator of the score of the comparison that comprises coloring the visual representation of the m/z segment with a color indicating the score.

14. The method of claim 10, further comprising labeling a visual representation of the m/z segment in a mass spectrogram with an indicator of the score of the comparison that comprises coloring the visual representation of the m/z segment with a numeric value of the score.

15. A non-transitory computer-readable storage medium storing a set of instructions capable of being executed by a processor, that when executed by the processor causes the processor to:
    concurrently display a chromatographic trace and a mass/charge (m/z) trace;
    receive a user-selected time period from the display of the chromatographic trace that includes a region of peak signal intensity;
    determine intensity values at a m/z segment for each of a plurality of times within the time period;
    compare a time course of the intensity values for the m/z segment over the time period to the time course of the chromatographic trace signal intensity over the region of peak signal intensity; and update the m/z trace with a visual representation of an indicator of a score of the comparison.

* * * * *